(12) United States Patent
Schattner et al.

(10) Patent No.: US 6,375,017 B1
(45) Date of Patent: Apr. 23, 2002

(54) TUBING ORGANIZER APPARATUS

(75) Inventors: Robert L. Schattner, Cherry Hill, NJ (US); Joseph Clarke, Hatboro; Kyle A. Jackson, Morrisville, both of PA (US); Robert A. Zera, Somerdale, NJ (US); Dennis A. Hart, Philadelphia, PA (US)

(73) Assignee: Omnimed Acquistion Corp, West Des Moines, IA (US)

( * ) Notice: Subject to any disclaimer, the term of this patent is extended or adjusted under 35 U.S.C. 154(b) by 0 days.

(21) Appl. No.: 09/534,499

(22) Filed: Mar. 24, 2000

(51) Int. Cl.$^7$ .................................................. A47F 5/00
(52) U.S. Cl. ..................... 211/85.13; 211/70; 248/68.1; 604/80
(58) Field of Search ........................ 248/68.1; 211/60.1, 211/85.13, 70; 604/80

(56) References Cited

U.S. PATENT DOCUMENTS

| | | | |
|---|---|---|---|
| 2,017,088 A | * 10/1935 | Bihler | |
| 3,116,730 A | * 1/1964 | Tingley | |
| 3,210,816 A | * 10/1965 | Clemons | |
| 3,472,389 A | * 10/1969 | Lowe | |
| D263,624 S | * 3/1982 | Stenzler et al. | |
| 4,971,271 A | * 11/1990 | Sularz | 248/68.1 |
| 4,988,062 A | * 1/1991 | London | 248/68.1 |
| 5,224,674 A | * 7/1993 | Simons | 248/68.1 |
| 5,316,246 A | * 5/1994 | Scott et al. | 248/68.1 |
| 5,427,338 A | * 6/1995 | Garrett et al. | 248/68.1 |
| 5,669,514 A | * 9/1997 | Massetti | |
| 5,678,348 A | * 10/1997 | Zielinski et al. | |
| 6,247,963 B1 | * 6/2001 | Rattner | 248/68.1 X |

* cited by examiner

Primary Examiner—Robert W. Gibson, Jr.
(74) Attorney, Agent, or Firm—Blank Rome Comisky & McCauley LLP

(57) ABSTRACT

A tubing organizer apparatus includes a body member that extends radially outwardly from a central axis. The body member has opposite surfaces and a peripheral wall that is disposed between the opposite surfaces to define a thickness and extends circumferentially about the central axis. The peripheral wall includes a plurality of exterior wall segments facing outwardly relative to the central axis and a plurality of interior wall segments connected to the exterior wall segments. The plurality of interior wall segments are configured to form a corresponding plurality of notches extending inwardly between consecutive ones of the exterior wall segments and into the body member relative to the central axis. The tubing organizer apparatus might also include a support structure sized and adapted for rotatably mounting the body member thereto. Also, the tubing organizer apparatus might include a plurality of gates with each gate spanning across a respective notch adjacent consecutive ones of the exterior wall segments. Each of the gates moves between an opened state and a closed state for releasably retaining one or more lengths of pliable tubing within the respective notch.

28 Claims, 8 Drawing Sheets

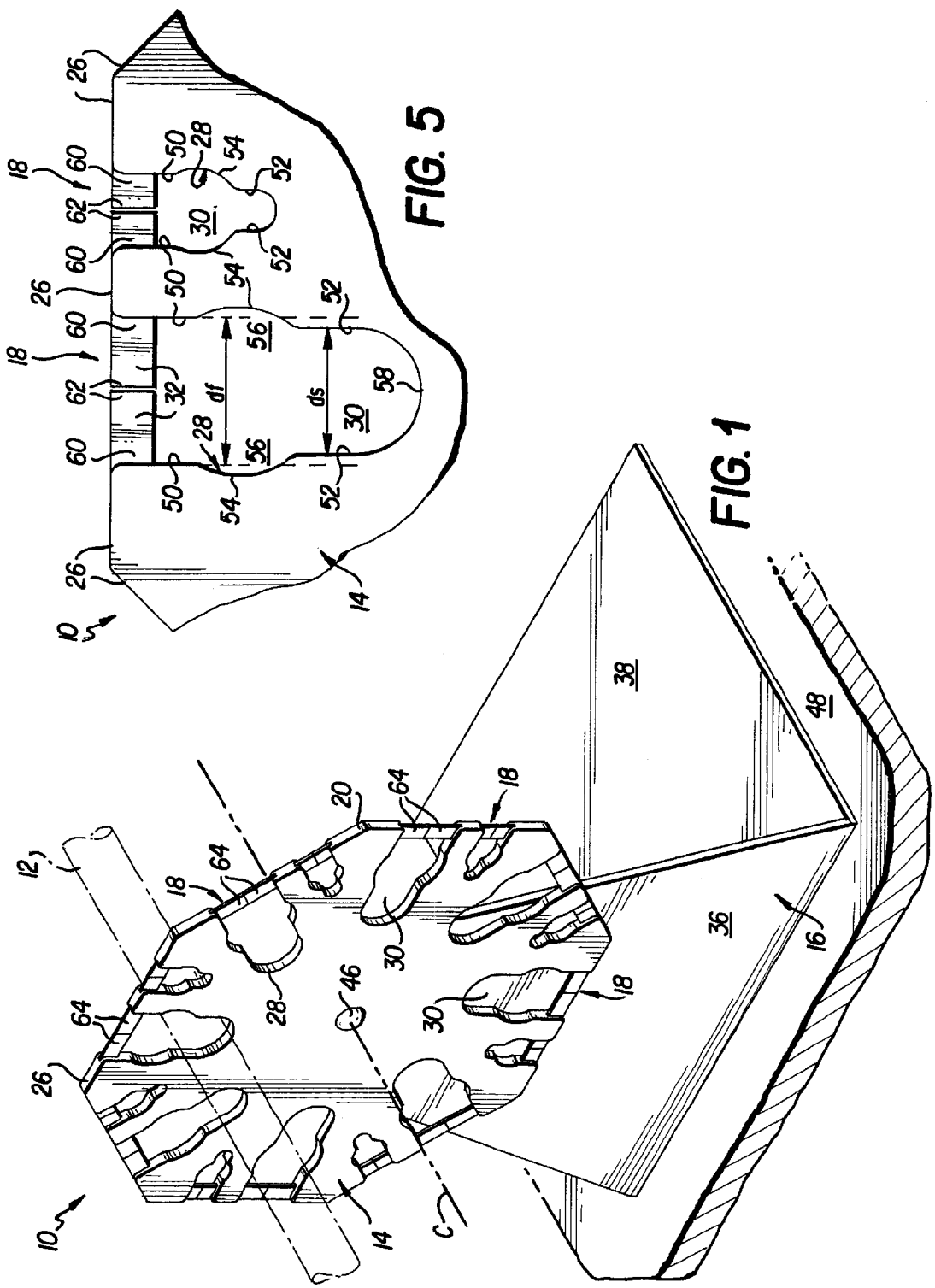

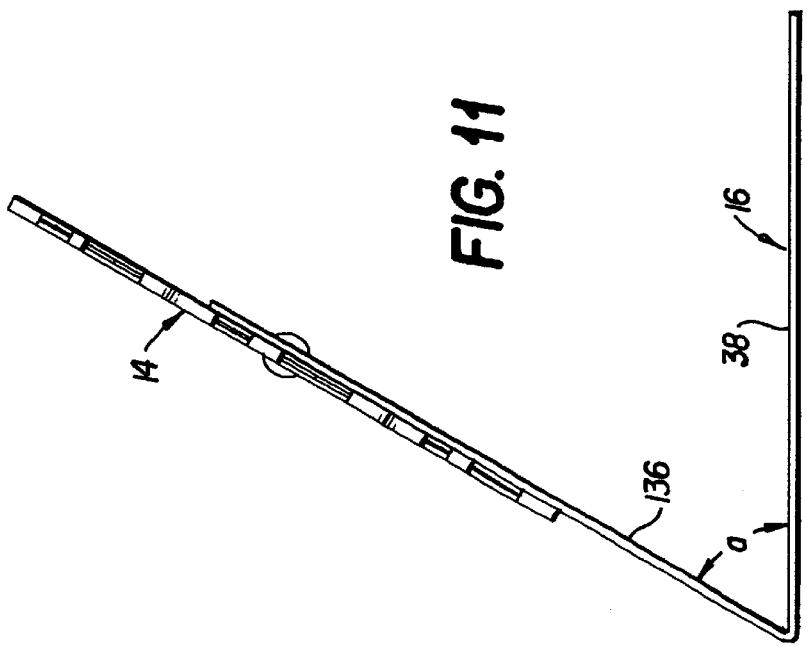
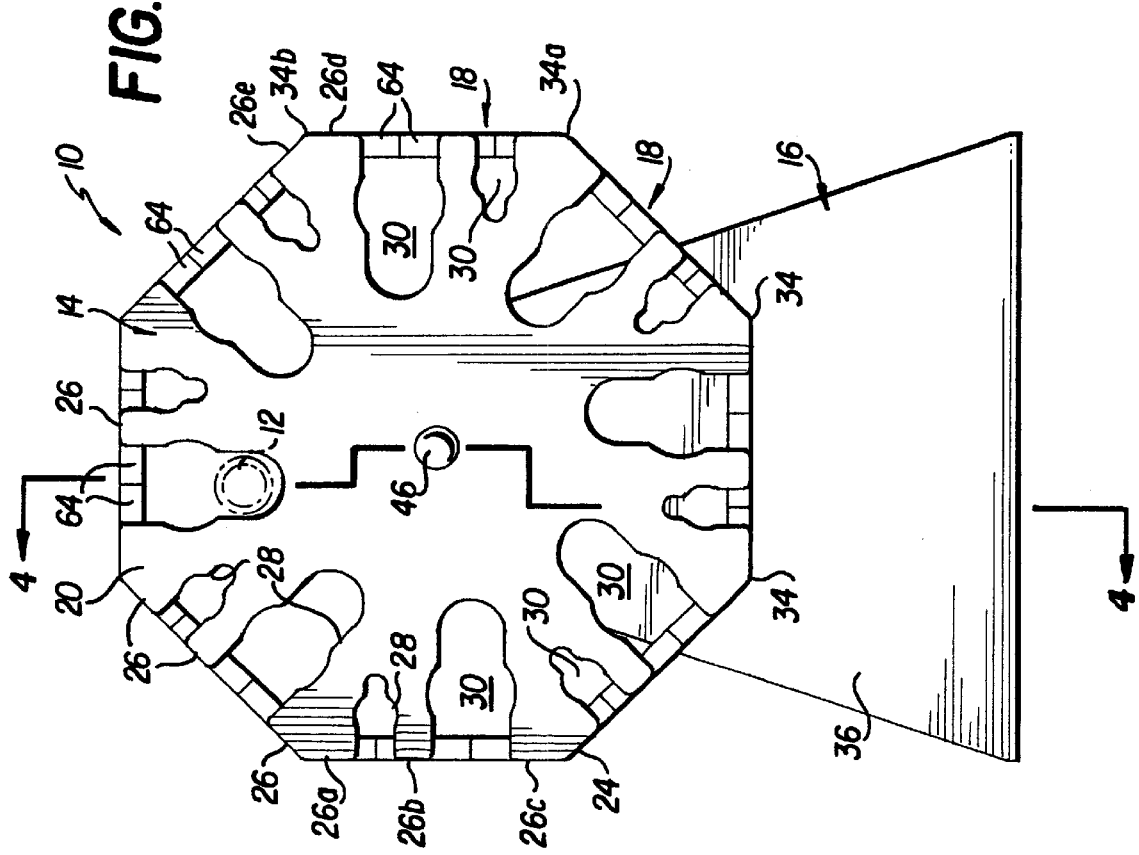

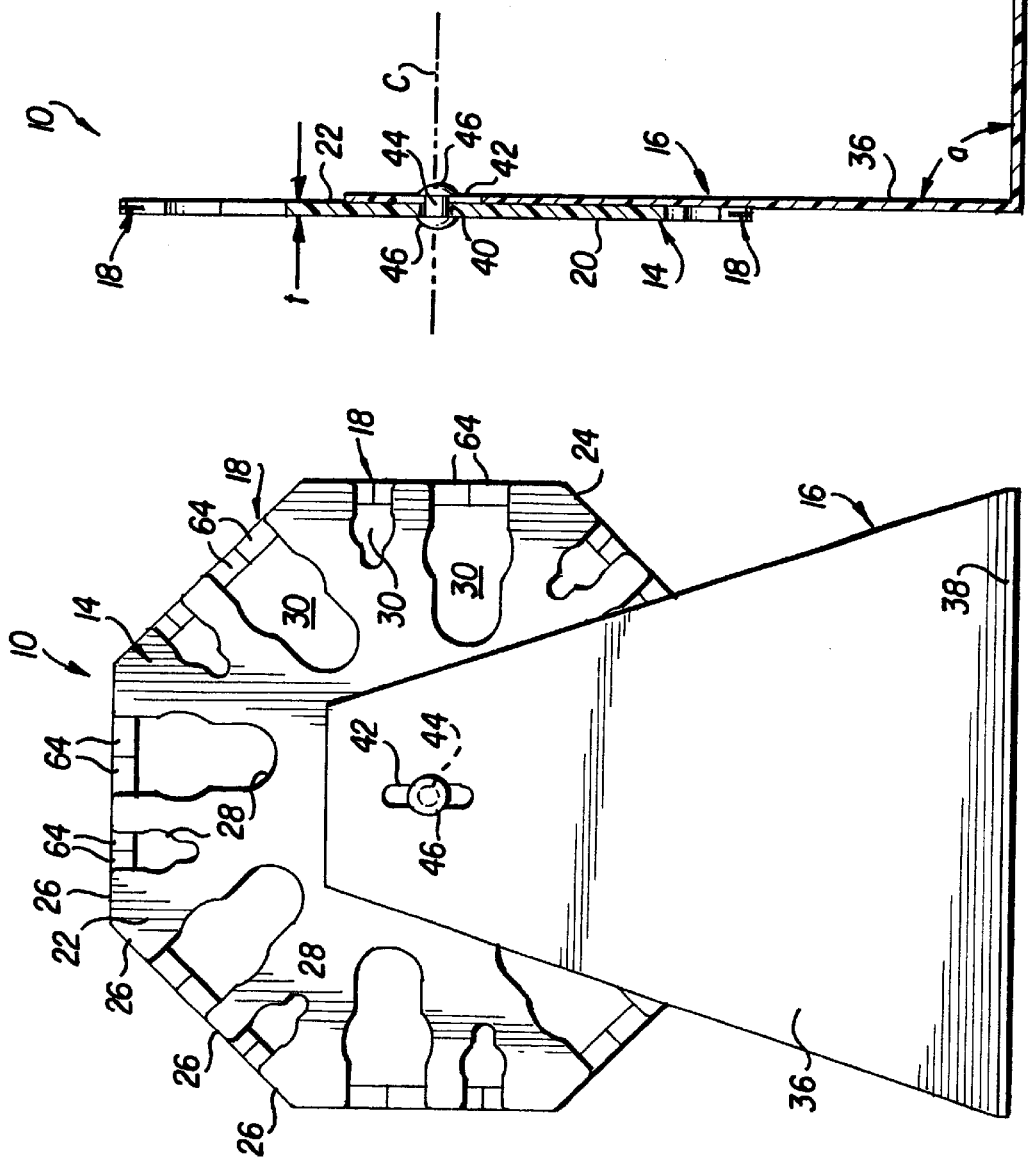

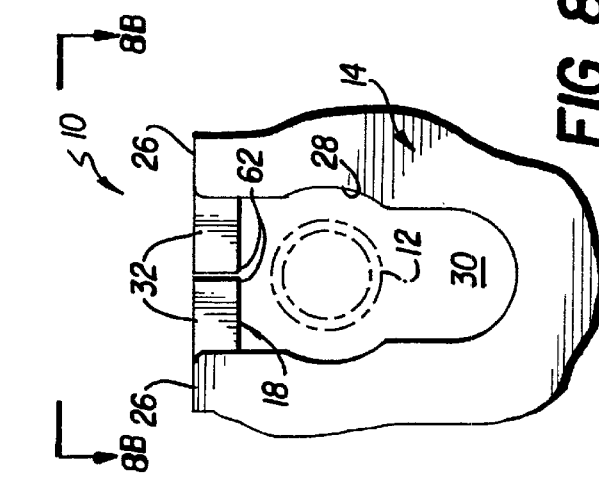
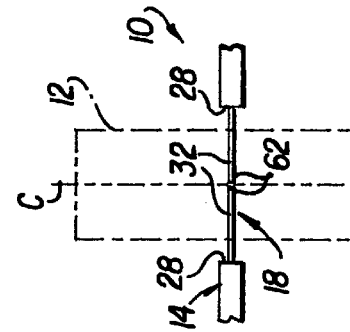
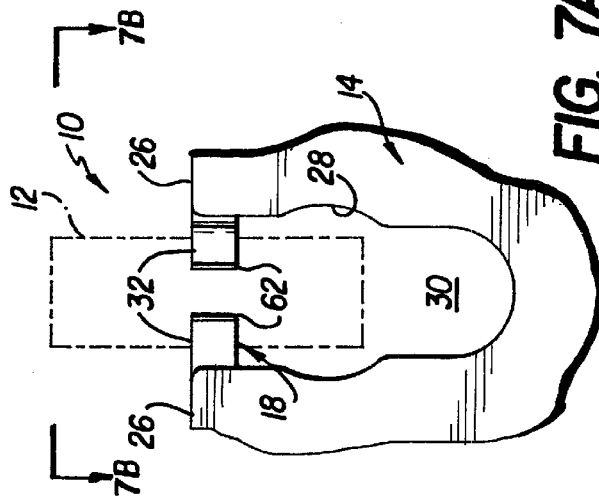
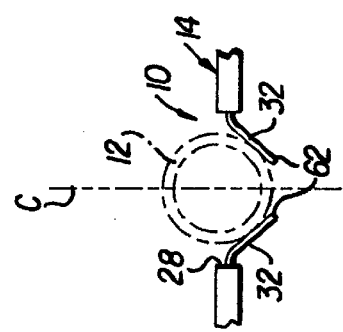
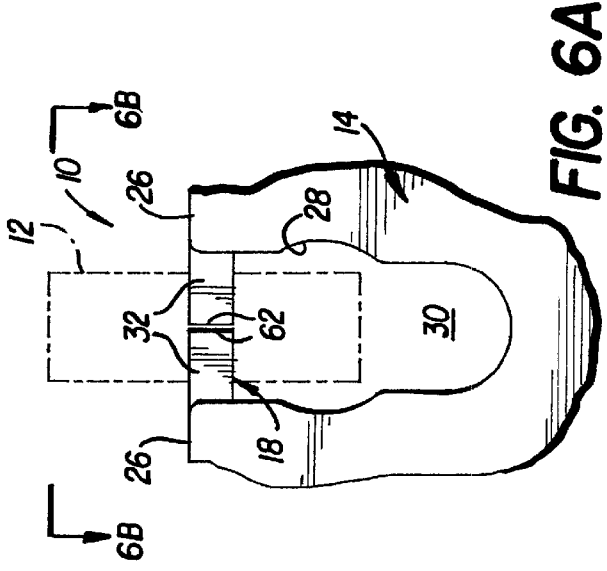
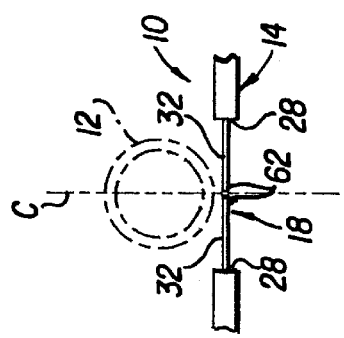

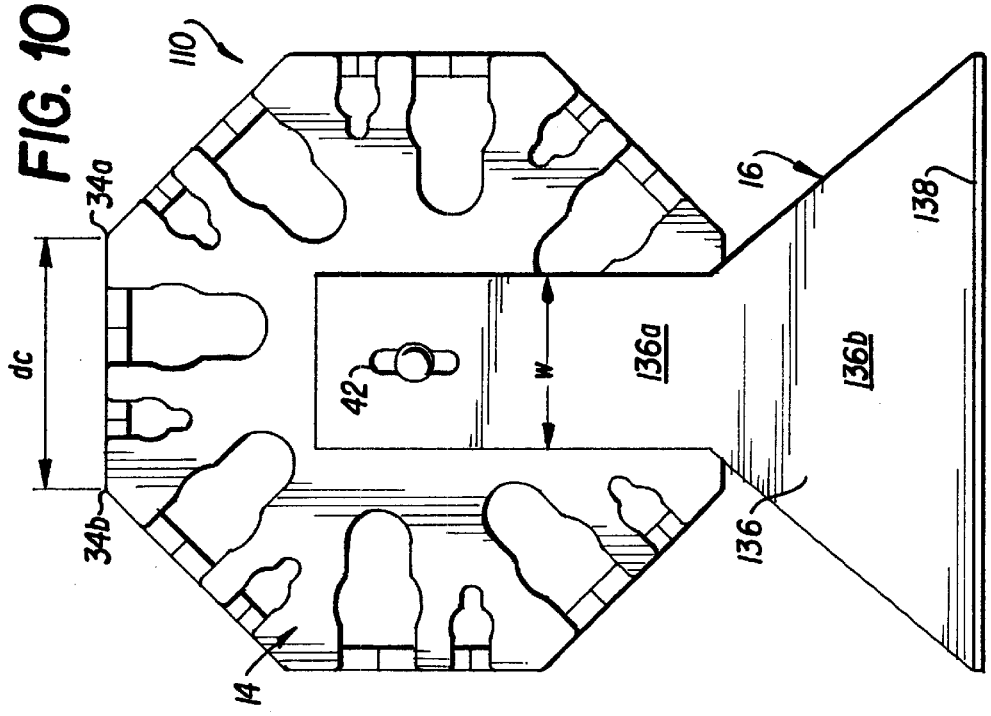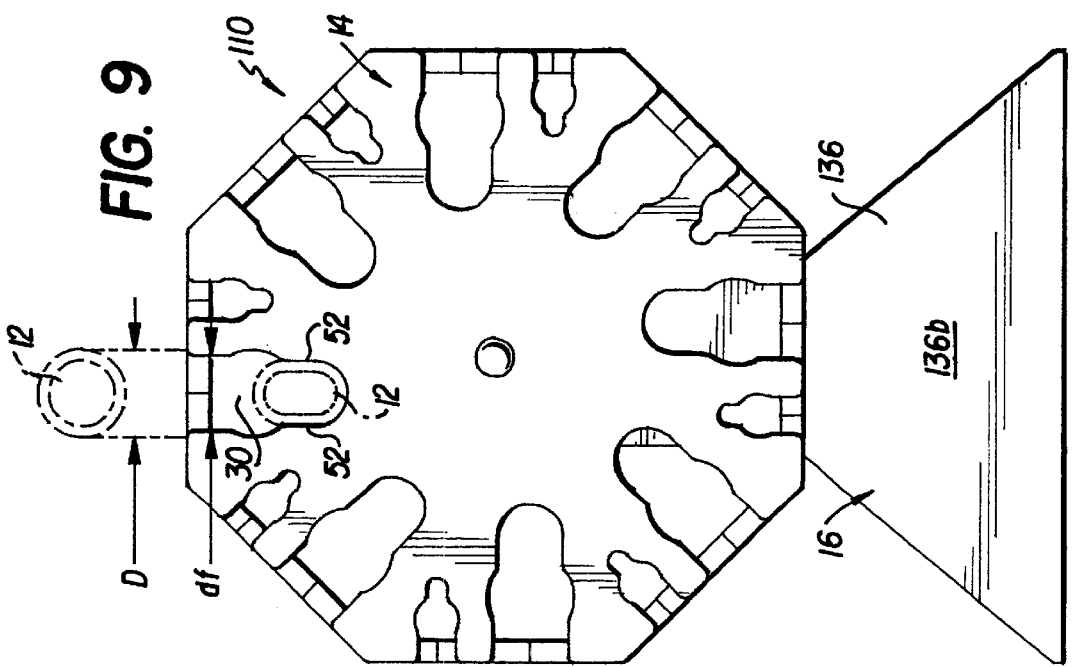

TUBING ORGANIZER APPARATUS

FIELD OF THE INVENTION

The invention relates to a tubing organizer apparatus. More particularly, the invention is directed to a tubing organizer apparatus that releasably retains one or more lengths of pliable tubing.

BACKGROUND OF THE INVENTION

In a hospital/healthcare environment, particularly in critical care or intensive care units, pliable tubing is often used to convey fluids into and from a patient. For example, medications may be supplied to the patient via tubes and bodily fluids may be withdrawn from the patient. Sometimes, such pliable tubing is either tied with a cord or taped to the patient's bed or other fixtures or hardware found in the room. In such situations, moving the patient requires untying the cord or removal of the tape before the patient can be moved. Unfastening the tubing from the bed or other fixture also consumes time which might be critical to the patient's well being.

Accordingly, it would be desirable to have a tubing organizer apparatus that can releasably retain one or more pliable tubes in an secure manner. It would also be beneficial to have such a tubing organizer apparatus that could releasably retain multiple lengths of pliable tubing in a well organized fashion so that a healthcare professional can ascertain and separate one length of tubing from another. It would also be beneficial if the tubing organizer apparatus were constructed to releasably retain multiple lengths of pliable tubing that have different tubing diameters. Additionally, it would be advantageous if such a tubing organizer apparatus was designed so that the pliable tubing can be easily connected thereto or removed therefrom.

The present invention is designed and constructed to provide the foregoing benefits, features and advantages as more fully described hereinafter.

OBJECT AND SUMMARY OF THE INVENTION

It is an object of the invention to provide a tubing organizer apparatus that is constructed to releasably retain one or more lengths of pliable tubing.

Another object of the invention is to provide a tubing organizer apparatus that releasably retains multiple lengths of tubing in a separately disposed, organized fashion.

Yet another object of the invention is to provide a tubing organizer apparatus that releasably retains multiple lengths of pliable tubing which may have different tubing diameters.

A still further object of the invention is to provide a tubing organizer apparatus that releasably retains multiple lengths of pliable tubing in either a loose fitting, close fitting or force fitting manner.

Yet another of the invention is to provide a tubing organizer apparatus onto which a length of pliable tubing can be easily connected to, or removed from, the tubing organizer apparatus.

A still further object of the invention is to provide a tubing organizer apparatus that releasably retains one or more lengths of pliable tubing in either a horizontal, vertical, or angular orientation.

Another object of the invention is to provide a tubing organizer apparatus that is of a simple design which may be economically manufactured by one or more conventional manufacturing processes.

Accordingly, the tubing organizer apparatus of the present invention as hereinafter described is especially constructed to accomplish the foregoing objects of the invention. The tubing organizer apparatus of the invention includes a substantially flat body member that extends radially outwardly from a central axis. The body member has opposite, preferably planar, surfaces and a peripheral wall disposed between the opposite surfaces to define a relatively thin thickness. The peripheral wall includes a plurality of exterior wall segments facing outwardly relative to the central axis and a plurality of interior wall segments connected to the exterior wall segments. The plurality of interior wall segments are configured to form a corresponding plurality of notches or cut outs that extend inwardly between consecutive ones of the exterior wall segments and into the body member relative to the central axis.

Another embodiment of the tubing organizer apparatus of the invention includes the body member and support structure. The support structure is sized and adapted for mounting the body member thereto for rotation about its central axis.

Another embodiment of the tubing organizer apparatus of the invention includes the body member, the support structure, and a plurality of gates. Preferably, each gate has a pair of finger elements. Each gate element is connected to respective interior wall segments and is operative to move to and between an opened state and a closed state. In the opened state, each one of the pair of finger elements of the gate element is moved outwardly from a respective notch allowing at least one pliable tube to pass into or out of the notch. In the closed state, the pair of finger elements span a respective notch adjacent and between consecutive ones of the exterior wall segments thereby retaining the pliable tube in such notch.

Other objects and advantages of the invention will become apparent from the following description of the exemplary embodiments of the invention taken in conjunction with the accompanying drawings.

BRIEF DESCRIPTION OF THE DRAWINGS

FIG. 1 is a perspective view of a first exemplary embodiment of a tubing organizer apparatus of the invention disposed on a horizontal support surface.

FIG. 2 is a front elevational view of the tubing organizer apparatus of the invention in FIG. 1.

FIG. 3 is a rear elevational view of the tubing organizer apparatus of the invention in FIG. 1.

FIG. 4 is a side elevational view taken in cross-section along line 4—4 in FIG. 2.

FIG. 5 is an enlarged partial front elevational detail view of a first notch and a second notch formed in a body member of the tubing organizer apparatus of the invention shown in FIG. 1.

FIG. 6A is an enlarged partial front elevational detail view of the body member with a length of pliable tubing before it enters the notch of the tubing organizer apparatus of the invention.

FIG. 6B is an enlarged partial side elevational detail view of the body member viewed from line 6B—6B in FIG. 6A.

FIG. 7A is an enlarged partial front elevational detail view of the body member with the pliable tubing entering into the notch through a gate comprising a pair of fingers.

FIG. 7B is an enlarged partial side elevational detail view of the body member viewed from line 7B—7B in FIG. 7A.

FIG. 8A is an enlarged partial front elevational detail view of the body member with the pliable tubing disposed in the notch of the tubing organizer apparatus of the invention.

FIG. 8B is an enlarged partial side elevational detail view of the body member viewed from line 8B—8B in FIG. 8A.

FIG. 9 is a front elevational view of a second exemplary embodiment of the tubing organizer apparatus of the invention.

FIG. 10 is a rear elevational view of the tubing organizer apparatus of the invention shown in FIG. 9.

FIG. 11 is a side elevational view of the tubing organizer apparatus of the invention shown in FIGS. 9 and 10.

DETAILED DESCRIPTION OF THE EXEMPLARY EMBODIMENTS

Figure 14:
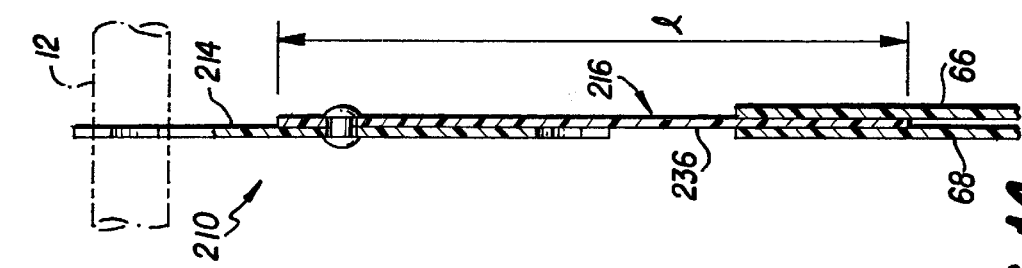
FIG. 14 is a side elevational view in cross-section of the tubing organizer apparatus of the invention shown in FIG. 12.

A first exemplary embodiment of a tubing organizer apparatus 10 of the invention is illustrated in FIGS. 1 to 8. The tubing organizer apparatus 10 of the invention releasably retains at least one length of pliable tubing 12. Preferably, the tubing organizer of the invention releasably retains a plurality of lengths of pliable tubing 12. For the first exemplary embodiment, the tubing organizer apparatus 10 of the invention comprises a body member 14, a support structure 16 and a plurality of gates or 18.

In FIG. 1, the body member 14 is a substantially flat plate member that extends radially outwardly from a central axis C. The body member 14 has opposite, substantially planar surfaces 20 and 22 (FIG. 4) and a peripheral wall 24. The peripheral wall 24 is disposed between the opposite surfaces 20 and 22 to define a thickness t as shown in FIG. 4 and extends circumferentially or peripherally about the central axis C. Also, the peripheral wall 24 includes a plurality of exterior wall segments 26 and a plurality of interior wall segments 28. The plurality of exterior wall segments 26 face outwardly relative to the central axis C, i.e., are on the peripheral wall 24. The plurality of interior wall segments 28 are connected to the exterior wall segments 26 and are configured to form a corresponding plurality of notches or cut outs 30 that are positioned between consecutive ones of the exterior wall segments 26. The plurality of notches 30 also extend inwardly into the body member 14 relative to the central axis C. Each one of the plurality notches 30 is sized to receive at least one pliable tube 12 as illustrated in FIG. 1 as well as in other figures hereinafter discussed.

The support structure 16 is connected to the body member 14. Particularly, the support structure 16 is formed as a stand for rotatably mounting the body member 14 thereto in a vertical plane as is discussed in more detail below.

Referring to FIG. 5, each gate 18 includes a pair of fingers 32. Each finger 32 is connected to a respective interior wall segment 28 as best shown in FIGS. 5–8. As illustrated in FIGS. 6A, 6B and 8A, 8B, each one of the pair of fingers 32 moves to and between an opened state (FIGS. 7A, 7B) and a closed stated (FIGS. 6A, 6B and 8A, 8B). In the opened state, each one of the pair of fingers 32 moves outwardly from the notch 30 which allows the pliable tube 12 to be placed into and removed from the notch 30. In the closed state, the pair of fingers 32 span the notch 30 adjacent and between the consecutive ones of the exterior wall segments 26 thereby retaining the pliable tube 12 in the notch 30. Note in FIG. 2, the pliable tubing 12 is releasably retained in the tubing organizer apparatus 10 of the invention in a relatively loose fitting relationship.

For the first exemplary embodiment of the tubing organizer apparatus 10 of the invention, the body member 14 is configured as a polygonal disk and, more specifically, as an octagonal disk, as shown in FIGS. 1–3. As specifically shown in FIG. 2, selected consecutive ones of the exterior wall segments, for example, 26a–c are arranged collinearly or coplanar with one another.

As is well known, an octagonal shaped disk, such as body member 14, has eight corners 34. The eight corners 34 connect non-collinear or non-coplanar ones of the exterior wall segments, for example, 26d and 26e, in FIG. 2. For the first exemplary embodiment of the tubing organizer apparatus 10 of the invention, two differently sized notches 30 are disposed between successive ones of the eight corners, for example, corners 34a and 34b. However, one of ordinary skill in the art will appreciate that at least one notch 30 is disposed between successive ones of the eight corners 34 and that more than two notches 30 may be disposed between corners 34.

In FIGS. 1–4, the support structure 16 includes a mounting panel member 36 and a base panel member 38 with body member 14 being rotatably mounted to the mounting panel member 36. Although not by way of limitation, the mounting panel member 36 is trapezoidal in configuration. As best shown in FIG. 4, body member 14 includes a hole 40 disposed along central axis C of the body member and extends between and through the opposite surfaces 20 and 22. Correspondingly, the mounting panel member 36 includes a mounting hole or slot 42 that extends therethrough. Although not by way of limitation, the mounting hole 42 may be formed as an elongated slot as shown. A shaft 44 connects the body member 14 and the mounting panel member 36 so that the body member 14 can be rotated relative to the support structure. The shaft 44 is sized and adapted to extend through and be received by the hole 40 in the body member 14 and the mounting hole 42 in the mounting panel member 36. The shaft 44 includes opposing end caps or fasteners 46 which are preferably sized and adapted to tightly secure the body member 14 to the mounting panel member 36, while permitting rotation of the body member 14 relative to the mounting panel member. For example, the shaft 44 may be a headed pin with a sliding grip nut pressed onto the end opposite the head of the pin. Also, the shaft 44 may be a thumb screw with a wing nut. Having a thumb screw and wing nut extending through the elongated slot, a user could adjust the body member 14 vertically relative to the mounting panel member 36. Also, an annular element might be formed integrally with the body member 14 about the central axis C resulting in the body member 14 to be mounted in a spaced apart relationship relative to the mounting panel member 36.

The base panel member 38 is connected to the mounting panel member 36 at a preferred angle α of approximately 90° as shown in FIG. 4. The body member 14 is rotatably mounted to the mounting panel member 36 at the upper, narrower portion of the mounting panel member 36 while the lower, broader portion of the mounting panel member 36 is connected to the base panel member 38. The base panel member 38 is sized and adapted for resting on a horizontal support surface 48, such as a table top or a floor, as illustrated in FIG. 1.

With reference to FIG. 5, each of the notches 30 is generally U-shaped with each of the interior wall segments 28 defining the configuration and size of each notch 30. It should be understood by one of ordinary skill in the art that, although the plurality of differently sized notches 30 are shaped similarly, a variety of different shapes are possible, several of which are described below. In the first exemplary embodiment of the tubing organizer apparatus 10 of the invention, the interior wall segments 28 of each notch 30 include a first pair of facially opposing straight interior wall portions 50. The straight interior wall portions 50 extend parallel relative to one another and are separated from one another by a first distance $d_f$ for the larger notch 30. Further, each of the interior wall segments 28 includes a second pair of facially opposing straight wall portions 52. The second pair of facially opposing straight wall portions 52 extend parallel to one another and are separated from one another by a second distance $d_s$ for the larger notch 30. The first distance $d_f$ and the second distance $d_s$ are different from one another, with the first distance $d_f$ being greater than the second distance $d_s$. However, as illustrated in phantom, the first distance $d_f$ and the second distance $d_s$ can be equal.

As shown in FIG. 5, each of the interior wall segments 28 also includes a pair of facially opposing arcuate wall portions 54. Each one of the arcuate wall portions 54 is disposed between respective ones of the first and second straight wall portions 50 and 52, respectively. Each pair of the arcuate wall portions 54 forms a pair of facially opposing arcuately shaped recesses 56 into respective ones of the notches 30. Each of the interior wall segments 28 includes a rearward wall portion 58. Although not by way of limitation, the rearward wall portion 58 can be either semi-circular or curved as shown for the first exemplary embodiment of the tubing organizer apparatus 10 of the invention.

In FIGS. 4–8, respective ones of the pair of fingers 32 are connected to respective ones of the interior wall segments 28 in an opposing relationship. Particularly, respective ones of the pair of fingers 32 project outwardly from the respective interior wall segments 28 toward each other and terminate at respective finger ends 62. In the closed state as shown in FIGS. 6A–6B and 8A–8B, the finger ends 62 face each other in an abutting relationship. In the opened state shown in FIGS. 7A–7B, the finger ends 62 are disposed slightly spaced from one another. When the fingers 32 move to and between the opened state and the closed state, each of the fingers 32 moves or flexes generally axially, that is in a direction parallel to the central axis C as best shown in FIG. 7B. Further, each of the fingers 32 in the opened state is resiliently biased towards the closed state. Thus, it is preferred that the fingers 32 are fabricated from a stiff yet resilient material such as plastic. Using a plastic material, it is preferred that the fingers 32 and the body member 14 are fabricated in a unitary construction, for example, by plastic molding as a one piece part or by bonding or laminating a plurality of sheets together. The thickness of the fingers 32 in the axial direction is preferably less than the overall thickness t of the body member 14 to enhance the resiliency of the fingers.

Again, with reference to FIGS. 1–3, each of the fingers 32 has an outer finger edge 64. Respective ones of the outer finger edges 64 face outwardly relative to the central axis C. Further, in the closed state, respective ones of the outer finger edges 64 of each pair of fingers 32 form a plane. Additionally, the plane formed by the outer finger edges 64 is coplanar with adjacent ones of the exterior wall segments, for example, 26a, 26b and 26c in FIG. 2.

A second exemplary embodiment of a tubing organizer apparatus 110 of the invention is illustrated in FIGS. 9–11. The tubing organizer apparatus 110 of the invention is similar to the first exemplary embodiment in that it includes the body member 14 and the support structure 16. However, the support structure 16 has a mounting panel member 136 having a rectangular portion 136a and a trapezoidal portion 136b. The rectangular portion 136a includes the mounting hole 42 and is thus used for rotatably mounting body member 14. The trapezoidal portion 136b is interposed between the rectangular portion 136a and the base panel member 38. The width w of the rectangular portion 136a is preferably less than the distance $d_c$ between successive corners 34a and 34b. It will be apparent to those of skill in the art that the smaller the width w, the greater the number of usable notches 30.

In FIG. 11, the mounting panel member 136 is connected to the base panel member 38 at an acute angle α for retaining the body member 14 at an angular orientation. Preferably, the acute angle α is in the approximate range of 45° to 90°. If desired, the support structure 16 of the invention maybe made of a sufficiently malleable material, such as thin sheet metal, that permits the mounting panel member to be bent relative to the base panel member 38 to any desired angle α and retained at that angle.

As shown in FIG. 9, one notch 30 receives the pliable tube 12 in a force fitted relationship. In this instance, the diameter D of the pliable tube 12 is greater than the first distance $d_f$. However, because the tube 12 is pliable, it can be received in the notch 30 and, by way of example, force fitted between the second pair or straight interior wall portions 52.

Figure 13:
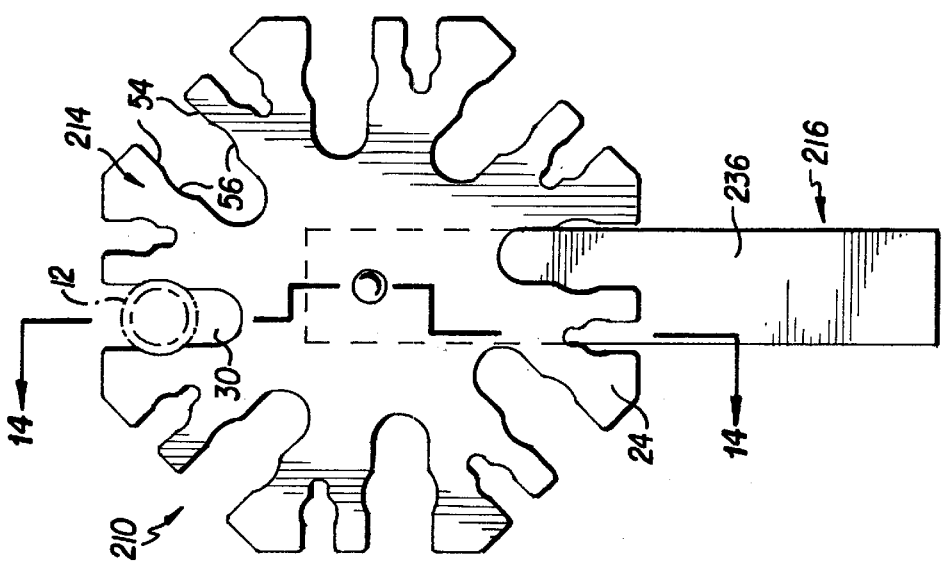
FIG. 13 is a front elevational view of the tubing organizer apparatus of the invention shown in FIG. 12.
Figure 12:
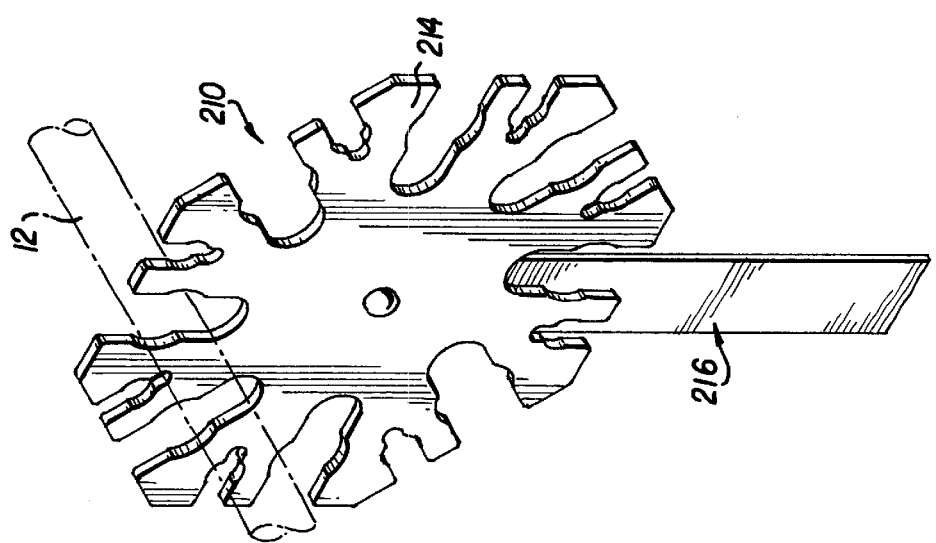
FIG. 12 is a perspective view of a third exemplary embodiment of the tubing organizer apparatus of the invention.

A third exemplary embodiment of a tubing organizer apparatus 210 of the invention is shown in FIGS. 12–14. The third exemplary embodiment of the tubing organizer apparatus 210 of the invention is similar to the embodiments described above, therefore, only the primary differences will be described. In the third exemplary embodiment, the body member 214 does not include fingers. Also, the support structure 216 only comprises a rectangularly-shaped mounting panel member 236 that projects beyond the peripheral wall 24 of the body member 214. The length l of the mounting panel member 236 as shown in FIG. 14 is sufficient so that the support structure 216 can be slidably received and retained between a pair of spaced support members 66 and 68. The support members 66 and 68 may be, for example, a pair of mattresses, such as vertically stacked mattresses so that the tubing organizer apparatus 210 is horizontally oriented, or a pair of side-by-side mattresses so that the tubing organizer apparatus 210 is vertically oriented. Of course, other forms of support members 66, 68 may be utilized to support the tubing organizer apparatus 210.

FIG. 13 shows the pliable tube 12 engaged in the notch 30 in a close fitting relationship between the pair of arcuate wall portions 54 and within arcuate recesses 56. Thus, in such a close fitting relationship, it is not essential to provide gates 18 with retaining fingers 32.

Figure 15:
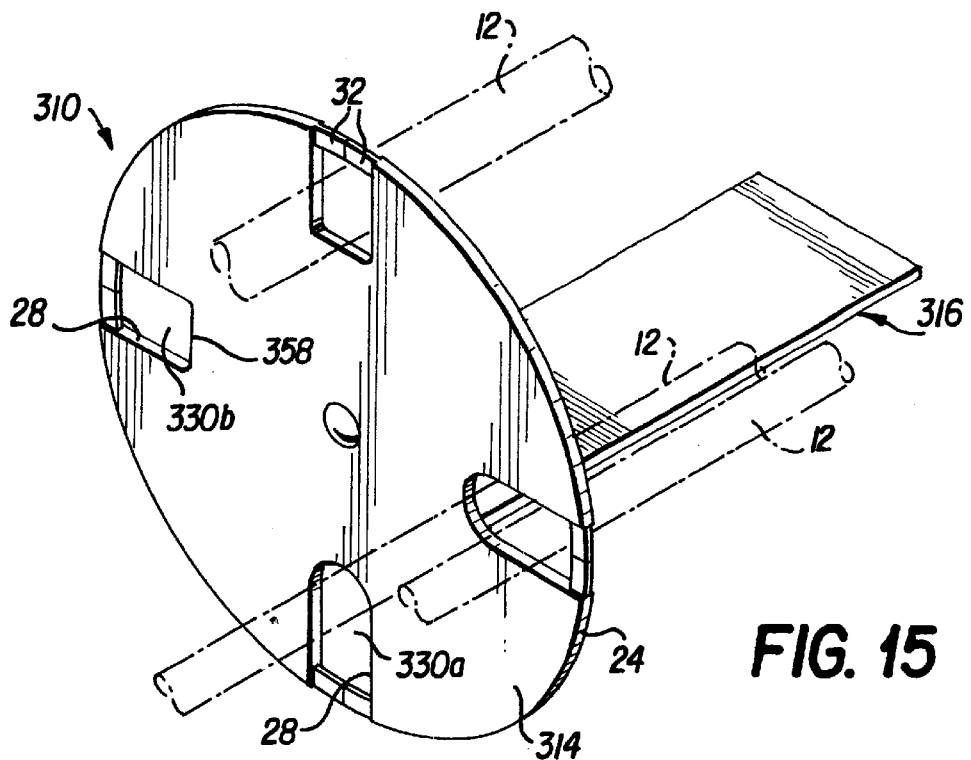
FIG. 15 is a perspective view of a fourth exemplary embodiment of the tubing organizer apparatus of the invention.
Figure 16:
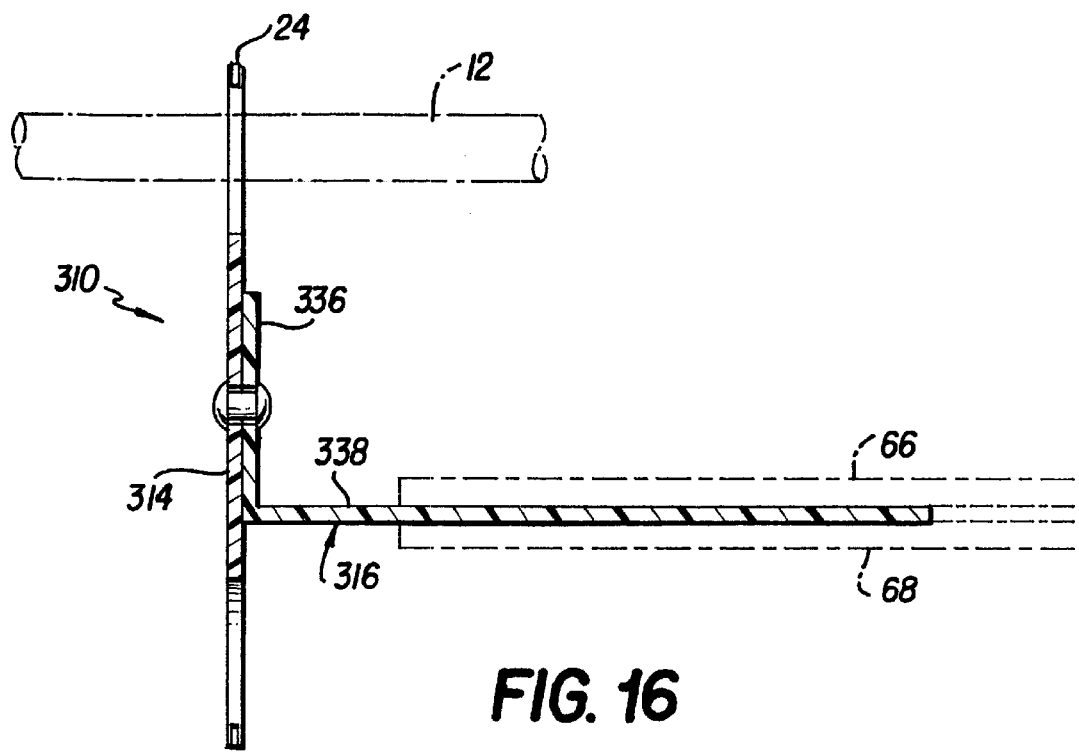
FIG. 16 is a side elevational view in cross-section of the tubing organizer apparatus of the invention shown in FIG. 15 disposed between stacked horizontal support structures.

A fourth exemplary embodiment of a tubing organizer apparatus 310 of the invention is illustrated in FIGS. 15 and 16. The tubing organizer apparatus 310 of the invention includes a circular body member 314 and a support structure 316. The body member 314 includes a plurality of U-shaped notches 330a and a plurality of rectangularly-shaped notches 330b. A rearward wall portion 58 of the interior wall segments 28 in each of the notches 330b is linear, thus forming the rectangularly shaped notches 330b.

The support structure 316 includes a mounting panel member 336 and a base panel member 338. Although not by way of limitation, the mounting panel member 336 does not extend radially beyond the circumferential wall 24 of the body member 314 so that all of the notches 330a–d are available to retain pliable tubing. The base panel member 338 is connected to the mounting panel member 336 and extends along a sufficient distance to be received between support members 66 and 68 to orient the body member 314 in a vertical plane. As shown in FIG. 15, multiple pliable tubes 12 can be received in any of the notches and retained therein by the fingers 32.

Figure 17:
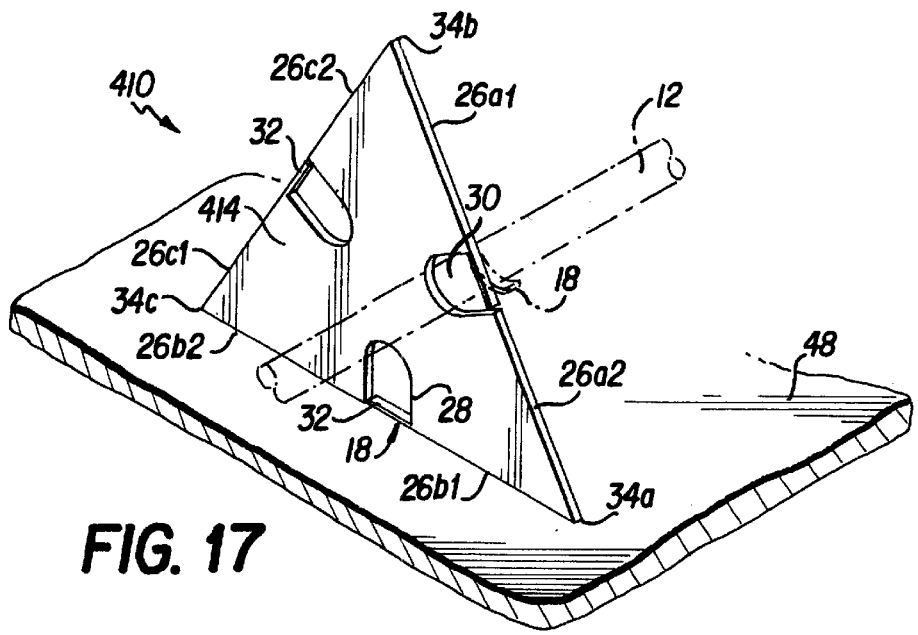
FIG. 17 is a fifth exemplary embodiment of the tubing organizer apparatus of the invention disposed on a horizontal support surface.

A fifth exemplary embodiment of a tubing organizer apparatus 410 of the invention is depicted in FIG. 17. The tubing organizer apparatus 410 of the invention includes a body member 414 and a plurality of gates 18 without a support structure. By way of example only, the body member 414 of the fifth exemplary embodiment is configured as a polygon in the shape of a triangle having three corners 34. Exterior wall segments 26 include exterior wall segments $26a_2$ and $26b_2$ connected by corner 34a; exterior wall segments $26a_2$ and $26c_2$ connected by corner 34b; and exterior wall segments $26b_1$ and $26c_1$ connected by corner 34c. Correspondingly, exterior wall segments $26a_1$ and $26a_2$ are coplanar with one another; exterior wall segments $26b_1$ and $26b_2$ are coplanar with one another; and exterior wall segments $26c_1$ and $26c_2$ are coplanar with one another.

Additionally, the tubing organizer apparatus 410 of the invention includes a plurality of gates 18. Rather than each gate 18 having a pair of fingers, the gates of tubing organizer apparatus 410 of the invention include only a single finger 32. Each single finger 32 is connected to a respective interior wall segment 28 and is operative to move to and between the opened state (gate 18 drawn in phantom in FIG. 17) and the closed state. It is preferred that the single finger 32 spans a respective notch 30 adjacent and between consecutive ones of the exterior wall segments, for example, $26a_1$ and $26a_2$. The single finger 32 retains the pliable tube 12 or multiple pliable tubes 12 within the notch 30. The tubing organizer apparatus 410 of the invention is particularly suitable for resting on a horizontal support surface 48 without the need for a support structure 16.

Figure 18:
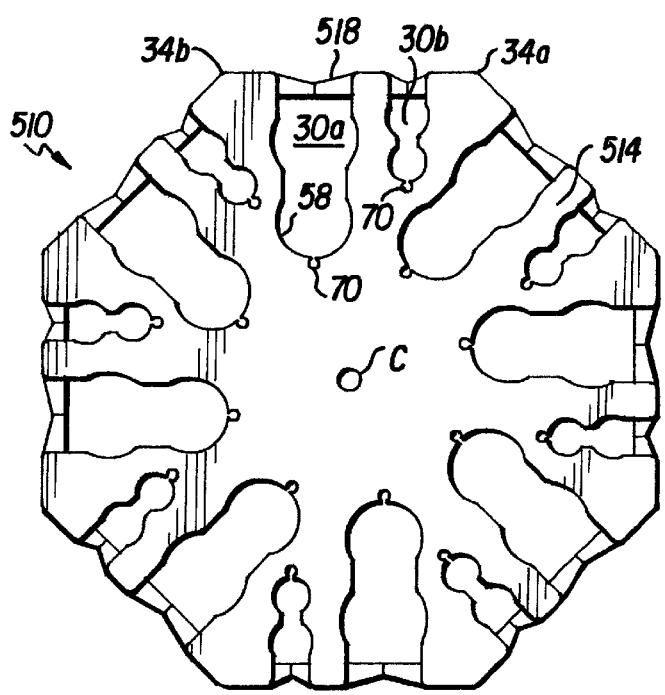
FIG. 18 is a front elevational view of a sixth exemplary embodiment of the tubing organizer apparatus of the invention.
Figure 19:
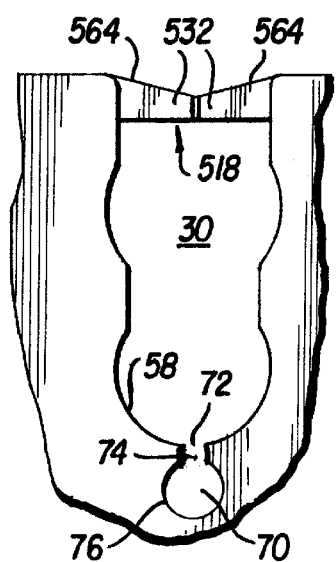
FIG. 19 is a partial front elevational detail view of the tubing organizer apparatus of the invention shown in FIG. 18.

A sixth exemplary embodiment of a tubing organizer apparatus 510 of the invention is depicted in FIGS. 18 and 19. The tubing organizer apparatus 510 of the invention includes a body member 514 and a plurality of gates 518. The body member 514 is formed, by way of example only, as an octagonal disk. The body member 514 includes two differently sized notches 30a and 30b, both of which are disposed between successive corners 34a and 34b, for example. Each of the notches 30a and 30b are configured generally in a manner as the first exemplary embodiment of the tubing organizer apparatus of the invention described above. Additionally, the rearward wall portion 58 includes a small circular cut out 70. The cut out 70 extends from the rearward wall portion 58 towards the central axis C.

As best shown in FIG. 19, the cut out 70 has an opening 72 that faces outwardly relative to the central axis C. Further, the cut out 70 includes a rectangularly shaped portion 74 that extends from the opening 72 and toward the central axis "C." Also, the cut out 70 has a generally circularly-shaped portion 76 that communicates with the rectangularly-shaped portion 74 to form a bulb-like configuration. The generally circularly-shaped portion 76 is sized to receive pliable tubing with small diameters.

Each gate 518 includes a pair of fingers 532 having outer finger edges 564. Respective ones of the outer finger edges 564 of each pair of fingers 532 form a V-shaped configuration on the periphery 524 of the body member 514.

One of ordinary skill in the art will appreciate that the tubing organizer apparatus described herein is useful with or without a support structure and can include differently sized and differently configured notches with or without gates. The tubing organizer apparatus enables a user to easily organize one or more lengths of tubing by inserting one or more lengths of tubing into the notches. The tubing organizer apparatus of the invention releasably retains multiple lengths of tubing in a spaced apart, organized fashion. Also, the tubing organizer apparatus releasably retains one or more lengths of pliable tubing regardless whether each length has a different tubing diameter. Further, the tubing organizer apparatus of the invention can be adapted to releasably retain one or more lengths of pliable tubing in either a loose fitting, close fitting, or force fitting manner and in either a horizontal, vertical or other angular orientation.

Although the exemplary embodiments of the invention have been specifically described herein, it would be apparent to those skilled in the art to which the invention pertains that other variations and modifications of the exemplary embodiments described herein maybe made without the departing from the spirit and scope of the invention.

What is claimed is:

1. A tubing organizer apparatus comprising a body member extending radially outwardly from a central axis and having opposite surfaces and a peripheral wall disposed between the opposite surfaces to define a thickness of the body member and extending about the central axis, the peripheral wall including a plurality of exterior wall segments facing outwardly relative to the central axis, a plurality of interior wall segments connected to the exterior wall segments and configured to form a corresponding plurality of notches extending inwardly between consecutive ones of the exterior wall segments and into the body member relative to the central axis, and a plurality of gates, each gate being connected to a respective interior wall segment and operative to move to and between an opened state wherein each gate moves outwardly from the respective notch allowing access into and out of the notch and a closed state wherein each gate spans a respective notch adjacent and between the consecutive ones of the exterior wall segments inhibiting access into and out of the notch.

2. A tubing organizer apparatus according to claim 1, wherein the peripheral wall of the body member is configured as a polygon.

3. A tubing organizer apparatus according to claim 2, wherein selected consecutive ones of the exterior wall segments are arranged collinearly with one another.

4. A tubing organizer apparatus according to claim 3, wherein when the body member is configured as a polygon having at least three corners connecting non-collinear ones of the exterior wall segments, at least one notch is disposed between successive ones of the at least three corners.

5. A tubing organizer apparatus according to claim 3, wherein when the body member is configured as a polygon having eight corners connecting non-collinear ones of the exterior wall segments, at least one notch is disposed between successive ones of the eight corners.

6. A tubing organizer apparatus according to claim 1, wherein each gate includes a pair of fingers, respective ones of the pair of fingers being connected to the interior wall segment in an opposing relationship and projecting outwardly from the interior wall segment towards each other to terminate in respective finger ends wherein in the closed state the finger ends face each other in an abutting relationship and wherein in the opened state the finger ends are disposed apart from one another.

7. A tubing organizer apparatus according to claim 6, wherein each of the fingers bends and is fabricated from a stiff yet resilient material.

8. A tubing organizer apparatus according to claim 7, wherein each of the fingers in the opened state are resiliently biased towards the closed state.

9. A tubing organizer apparatus according to claim 6, wherein each finger has an outer finger edge facing outwardly relative to the central axis and, in the closed state, respective ones of the outer finger edges of each pair of fingers form one of a straight line or an inwardly receding V-shaped configuration relative to the central axis.

10. A tubing organizer apparatus according to claim 1, wherein when the gate moves between the opened state and the closed state, the gate moves generally axially relative to the central axis.

11. A tubing organizer apparatus according to claim 1, wherein the plurality of gates and the body member are a unitary construction.

12. A tubing organizer apparatus according to claim 1, wherein the each of the plurality of notches is generally one of rectangularly shaped and U-shaped.

13. A tubing organizer apparatus according to claim 1, wherein each of the interior wall segments includes a first pair of facially opposing straight interior wall portions extending parallel to one another and separated from one another by a first distance.

14. A tubing organizer apparatus according to claim 13, wherein each of the interior wall segments includes a second pair of facially opposing straight wall portions extending parallel to one another and separated from one another by a second distance.

15. A tubing organizer apparatus according to claim 14, wherein the first distance and the second distance are one of equal to each other and different from one another with the first distance being greater than the second distance.

16. A tubing organizer apparatus according to claim 15, wherein each of the interior wall segments includes a pair of facially opposing arcuate wall portions, each arcuate wall portion disposed between respective ones of the first and second straight wall portions and forming a pair of facially opposing arcuately shaped recesses into respective ones of the plurality of notches.

17. A tubing organizer apparatus according to claim 15, wherein each of the interior wall segments includes a rearward wall portion interconnecting the pair of second wall segments, the rearward wall portion is one of straight, semi-circular and curved.

18. A tubing organizer apparatus according to claim 17, wherein the rearward wall portion includes an cut out formed thereinto and towards the cental axis, the cut out having an cut out opening facing outwardly relative to the cental axis, a rectangularly-shaped portion extending from the cut out opening and toward the central axis and a generally circularly-shaped portion connected to the rectangularly-shaped portion to form a bulb-like configuration.

19. A tubing organizer apparatus according to claim 1, wherein the body member is configured as a circle.

20. A tubing organizer apparatus, comprising:
a body member extending radially outwardly from a central axis and having opposite surfaces and a peripheral wall disposed between the opposite surfaces to define a thickness and extending circumferentially about the central axis, the peripheral wall including a plurality of exterior wall segments facing outwardly relative to the central axis and a plurality of interior wall segments connected to the exterior wall segments and configured to form a corresponding plurality of notches extending inwardly between consecutive ones of the exterior wall segments and into the body member relative to the central axis;
a plurality of gates, each gate being connected to a respective interior wall segment and operative to move to and between an opened state wherein each gate moves outwardly from the respective notch allowing access into and out of the notch and a closed state wherein each gate spans a respective notch adjacent and between the consecutive ones of the exterior wall segments inhibiting access into and out of the notch; and
a support structure sized and adapted for rotatably mounting the body member thereto.

21. A tubing organizer apparatus according to claim 20, wherein the support structure includes a mounting panel member, the body member being rotatably mounted to the mounting panel member.

22. A tubing organizer apparatus according to claim 21, wherein the support structure includes a base panel member connected to the mounting panel member and extending therefrom at an angle selected from an approximate range of 90 degrees and 45 degrees.

23. A tubing organizer apparatus according to claim 22, wherein the support structure has one of the base panel member sized and adapted for resting on a horizontal support surface and the mounting panel member sized to be slidably received between a pair of facially engaging support members.

24. A tubing organizer apparatus according to claim 20, wherein each gate includes a pair of fingers, respective ones of the pair of fingers being connected to the interior wall segment in an opposing relationship and projecting outwardly from the interior wall segment towards each other to terminate in respective finger ends wherein in the closed state the finger ends face each other in an abutting relationship and wherein in the opened state the finger ends are disposed apart from one another.

25. A tubing organizer apparatus according to claim 20, wherein the body member includes a hole disposed about the central axis and extending between and through the opposite surfaces and the mounting panel member includes a mounting hole extending therethrough.

26. A tubing organizer apparatus according to claim 25, further comprising a shaft connected to the body member and the mounting panel member wherein the shaft is sized and adapted to extend through and be received by hole in the body member and the mounting hole in the mounting panel member.

27. A tubing organizer apparatus for releasably retaining at least one pliable tube, comprising:
a body member extending radially outwardly from a central axis and having opposite surfaces and a peripheral wall disposed between the opposite surfaces to define a thickness and extending circumferentially about the central axis, the peripheral wall including a plurality of exterior wall segments facing outwardly relative to the central axis and a plurality of interior wall segments connected to the exterior wall segments and configured to form a corresponding plurality of notches extending inwardly between consecutive ones of the exterior wall segments and into the body member relative to the central axis, each one of the plurality of notches being sized to receive the at least one pliable tube;

a support structure sized and adapted for rotatably mounting the body member thereto; and a plurality of gates with each gate having a pair of fingers with each finger connected to a respective interior wall segment and operative to move to and between an opened state wherein each one of the pair of fingers moves outwardly from a respective notch allowing the at least one pliable tube access into and out of the notch and a closed state wherein the pair of fingers spans a respective notch adjacent and between the consecutive ones of the exterior wall segments inhibiting the at least one pliable tube from access into and out of the notch.

28. A tubing organizer apparatus according to claim 27, wherein respective ones of the pair of fingers are connected to the interior wall segment in an opposing relationship and projecting outwardly from the interior wall segment towards each other to terminate in respective finger ends wherein in the closed state the finger ends face each other in an abutting relationship and wherein in the opened state the finger ends are disposed apart from one another.

* * * * *